(12) United States Patent
Clemen, Jr.

(10) Patent No.: US 10,099,465 B2
(45) Date of Patent: Oct. 16, 2018

(54) COMPOSITE LAMINATE ENABLING STRUCTURAL MONITORING USING ELECTROMAGNETIC RADIATION

(71) Applicant: The Boeing Company, Chicago, IL (US)

(72) Inventor: Mark J. Clemen, Jr., Bremerton, WA (US)

(73) Assignee: The Boeing Company, Chicago, IL (US)

(*) Notice: Subject to any disclaimer, the term of this patent is extended or adjusted under 35 U.S.C. 154(b) by 192 days.

(21) Appl. No.: 14/312,668

(22) Filed: Jun. 23, 2014

(65) Prior Publication Data

US 2014/0302275 A1 Oct. 9, 2014

Related U.S. Application Data

(62) Division of application No. 13/344,182, filed on Jan. 5, 2012, now Pat. No. 8,771,443.

(51) Int. Cl.
| | |
|---|---|
| *B32B 5/12* | (2006.01) |
| *B32B 37/18* | (2006.01) |
| *B29C 65/82* | (2006.01) |
| *G01N 22/02* | (2006.01) |
| *B32B 7/02* | (2006.01) |

(Continued)

(52) U.S. Cl.
CPC .......... *B32B 37/18* (2013.01); *B29C 65/8253* (2013.01); *B32B 5/12* (2013.01); *B32B 7/02* (2013.01); *B32B 27/08* (2013.01); *B32B 27/12* (2013.01); *B32B 27/38* (2013.01); *B32B 41/00* (2013.01); *G01N 22/02* (2013.01); *B32B 2262/108* (2013.01); *B32B 2307/212* (2013.01); *B32B 2307/418* (2013.01); *B32B 2307/732* (2013.01); *B32B 2605/18* (2013.01); *Y10T 428/24058* (2015.01); *Y10T 428/2495* (2015.01); *Y10T 428/24124* (2015.01); *Y10T 428/24942* (2015.01); *Y10T 428/31511* (2015.04)

(58) Field of Classification Search
CPC .................................................. B32B 37/18
USPC ......................................... 428/411.1; 356/369
See application file for complete search history.

(56) References Cited

U.S. PATENT DOCUMENTS 4,622,254 A * 11/1986 Nishimura ............ B29C 70/228
                                                                            428/102
5,024,399 A *  6/1991 Barquet .................. B29C 70/44
                                                                            244/119

(Continued)

FOREIGN PATENT DOCUMENTS

JP            04251714 A  *  9/1992

OTHER PUBLICATIONS

Zong et al., "Dielectric analysis of a crosslinking epoxy resin at a high microwave frequency," Journal of Polymer Science Part B: Polymer Physics, vol. 42, Issue 15, Aug. 2004, pp. 2871-2877 (full article replaces abstract filed Jun. 14, 2013).

(Continued)

*Primary Examiner* — Brent T O'Hern
(74) *Attorney, Agent, or Firm* — Yee & Associates, P.C.

(57) ABSTRACT

Electromagnetic radiation scanning is used to monitor the integrity of a composite laminate structure. The composite laminate structure is optically resonant at a frequency of electromagnetic radiation, allowing inconsistencies in the laminate to be detected and mapped.

21 Claims, 5 Drawing Sheets

(51) Int. Cl.
*B32B 41/00* (2006.01)
*B32B 27/08* (2006.01)
*B32B 27/12* (2006.01)
*B32B 27/38* (2006.01)

(56) References Cited

U.S. PATENT DOCUMENTS

| | | | |
|---|---|---|---|
| 5,886,534 | A | 3/1999 | Bakhtiari et al. |
| 6,359,446 | B1 | 3/2002 | Little, Jr. |
| 6,462,561 | B1 | 10/2002 | Bigelow et al. |
| 7,439,749 | B2 | 10/2008 | Zoughi et al. |
| 8,771,443 | B2 | 7/2014 | Clemen, Jr. |
| 2006/0292375 | A1* | 12/2006 | Martin ............... B32B 5/28 428/413 |
| 2007/0007384 | A1* | 1/2007 | Sliwa, Jr. ......... B64D 45/0015 244/30 |
| 2008/0129316 | A1 | 6/2008 | Zoughi et al. |
| 2008/0230652 | A1* | 9/2008 | Biornstad ............ B29C 53/587 244/120 |
| 2009/0026315 | A1* | 1/2009 | Edelmann ........... B29C 70/205 244/119 |
| 2010/0133039 | A1* | 6/2010 | Liguore .............. B32B 5/26 181/294 |
| 2010/0260926 | A1 | 10/2010 | Wolfe et al. |
| 2011/0086199 | A1* | 4/2011 | Duqueine ........... B29C 70/202 428/112 |

OTHER PUBLICATIONS

Zong et al., "Dielectric studies of three epoxy resin systems during microwave cure," Polymer, vol. 46, Issue 8, Mar. 2005, pp. 2638-2645 (full article replaces abstract filed Jun. 14, 2013).
Shimabukuro et al., "Measurement of the Complex Dielectric Constant of Casting Resins at Millimeter Wavelengths Low-Loss," 1984 IEEE MTI-S International Microwave Symposium Digest, May-Jun. 1984, pp. 520-521 (full article replaces abstract filed Jun. 14, 2013).
Bolivar et al., "Measurement of the Dielectric Constant and Loss Tangent of High Dielectric-Constant Materials at Terahertz Frequencies," IEEE Transactions on Microwave Theory and Techniques, vol. 51, No. 4, Apr. 2003, pp. 1062-1066.
UK search report dated May 20, 2013 regarding application 881222874.8, reference P56337GB/RGH, applicant The Boeing Company, 5 pages.
"Anti-Reflective Coating,""Wikipedia, the free encyclopedia, Apr. 2013, 8 pages, accessed Jun. 14, 2013,http:ffen.wikipedia.org/wi kif Anti-reflective_ coating".
Krepelka, "Maximally flat antireflection coatings," Jemna Mechanika A Optika, vol. 3, May 1992, pp. 53-56.
Zong et al., "Dielectric analysis of a crosslinking epoxy resin at a high microwave frequency," Journal of Polymer Science Part B: Polymer Physics, vol. 42, Issue 15, Aug. 2004, pp. 2871-2877 (abstract).
Zong et al., "Dielectric studies of three epoxy resin systems during microwave cure," Polymer, vol. 46, Issue 8, Mar. 2005, pp. 2638-2645 (abstract).
Shimabukuro et al., "Measurement of the Complex Dielectric Constant of Casting Resins at Millimeter Wavelengths Low-Loss," 1984 IEEE MTI-S International Microwave Symposium Digest, May-Jun. 1984, pp. 520-521 (abstract).
Zhou et al., "Broadband Complex Permittivity Measurement of Low Loss Materials Over Large Temperature Ranges by Stripline Resonator Cavity Using Segmentation Calculation Method," Progress in Electromagnetics Research, vol. 113, Jan. 2011, pp. 143-160.
Office action dated Dec. 17, 2013 regarding U.S. Appl. No. 13/344,182, 13 pages.
Notice of Allowance dated Feb. 28, 2014 regarding U.S. Appl. No. 13/344,182, 8 pages.

\* cited by examiner

COMPOSITE LAMINATE ENABLING STRUCTURAL MONITORING USING ELECTROMAGNETIC RADIATION

This application is a divisional application of U.S. application Ser. No. 13/344,182, filed Jan. 5, 2012, issued as U.S. Pat. No. 8,771,443 on Jul. 8, 2014.

BACKGROUND INFORMATION

1. Field

The present disclosure generally relates to the detection of inconsistencies in composite laminate structures, especially those structures used in the aerospace industry, and deals more particularly with a laminate design and a method of monitoring laminate structures using electromagnetic radiation.

2. Background

It is sometimes desirable to detect inconsistencies in composite laminate structures that may affect the performance of the structure. Inconsistencies may occur in composite laminates at the time of manufacture, or later from events as such impacts after the structure has been placed in service. Some of these inconsistencies may become pronounced over time and thus may require monitoring.

A variety of non-destructive evaluation (NDE) techniques have been developed for identifying the occurrence and frequency of inconsistencies in composite laminates, such as composite components used in aircraft. These techniques include ultra-sound, forward x-ray absorption imaging, and backward x-ray scatter imaging. However, these known techniques relatively slow, difficult to implement in the field and may gather limited information.

Accordingly, there is a need for a composite laminate design that enables rapid detection of internal inconsistencies in the laminate. There is also a need for a method of quickly detecting inconsistencies in composite laminates over a wide area of a structure, and which allows differentiation between different types of inconsistencies.

SUMMARY

The disclosed embodiments provide a composite laminate design enabling the integrity of a composite laminate structure to be certified and requalified throughout its service life. The composite laminate is designed to be substantially completely reflective or non-reflective to electromagnetic (EM) energy at one or more specified design frequencies, except in the presence of an inconsistency in the laminate.

The disclosed embodiments also provide a method of detecting inconsistencies in the designed laminate by scanning the laminate with an EM source, detecting EM signals reflected from the laminate during the scan, and mapping the reflected signals to assess the overall integrity of the structure. The disclosed method allows rapid detection of relatively small inconsistencies over relatively large areas of a composite laminate structure that may be created during the manufacturing process, or develop later when the structure has been placed in service. The detection process uses short wavelength microwaves that may allow inconsistencies to be detected, even with millimeter scale resolution. In one embodiment, laminate layers of chosen thicknesses and resins form a resonant stack at two preselected frequencies of EM energy that becomes sensitive to a variety of lamina inconsistencies. The method may further comprise selecting a particular microwave scanning polarization and phase to be most-sensitive or least-sensitive to carbon fiber reinforcement layers of a laminate structure.

According to one disclosed embodiments, a method is provided of fabricating a composite laminate enabling detection of inconsistencies in the laminate using electromagnetic radiation scanning. The method comprises laminating a stack of at least two resin layers, selecting an approximate thickness of each of the two layers based on a preselected electromagnetic frequency, and selecting a resin for each of the resin layers that results the laminated stack being substantially resonant at the preselected frequency. Selecting the approximate thickness of each of the two resin layers includes calculating the thickness of the layer based on the number of the layers in the stack. Selecting the resin includes determining indices of refraction of the resins that cause each of the layers to be anti-reflective. The method may further comprise placing unidirectional reinforcement fibers between the layers, and optimizing the orientation of reinforcement fibers. The method may further comprise correcting each of the determined indices of refraction for absorption of the electromagnetic energy in the resin layers.

According to another embodiment, a composite laminate is provided enabling detection of inconsistencies in the laminate using electromagnetic radiation scanning. The laminate comprises a laminated stack of resin layers configured to resonate at the frequency of the electromagnetic radiation, wherein inconsistencies in the laminate result in disruption the resonance that is detectable by the radiation scanning. Each of the resin layers may have a thickness that results in the stack being substantially anti-reflective to electromagnetic radiation of a wavelength within the microwave range.

According to still another embodiment, a method is provided of detecting inconsistencies in a composite laminate, comprising fabricating a laminate to resonate at either of two preselected electromagnetic frequencies; interrogating the laminate with circularly polarized radiation of the preselected frequencies; receiving and recording an electromagnetic energy signature reflected from the laminate; and identifying inconsistencies in the laminate by comparing the received signature with a design signature. The method may further comprise generating a pair of images of the laminate representing the results of the comparison of the signatures respectively at the two preselected frequencies.

BRIEF DESCRIPTION OF THE DRAWINGS

The novel features believed characteristic of the advantageous embodiments are set forth in the appended claims. The advantageous embodiments, however, as well as a preferred mode of use, further objectives and advantages thereof, will best be understood by reference to the following detailed description of an advantageous embodiment of the present disclosure when read in conjunction with the accompanying drawings, wherein:

DETAILED DESCRIPTION

Figure 1:
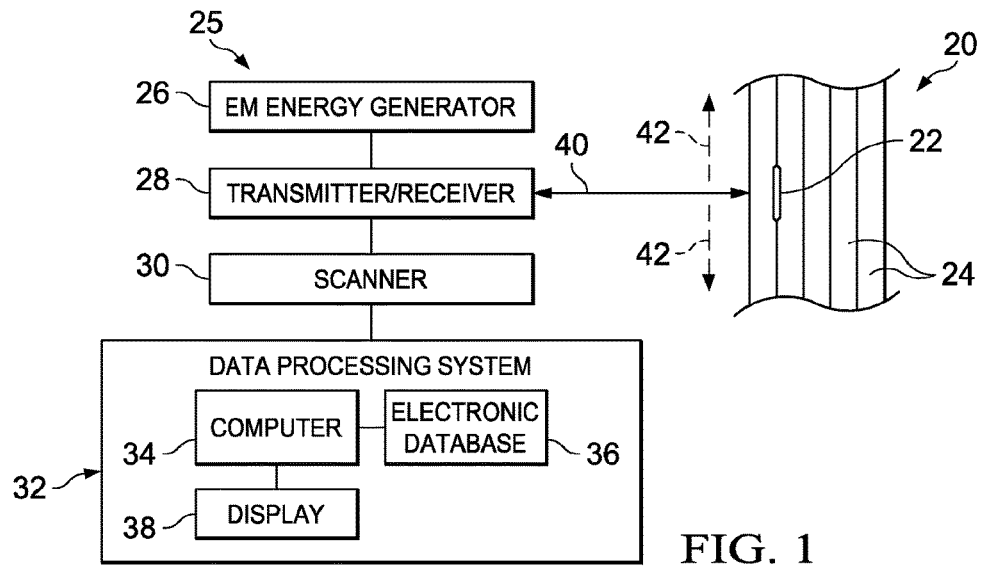
FIG. 1 is a combined cross sectional view of a composite laminate, and block diagram of apparatus for structural evaluation of the laminate.

Referring first to FIG. 1, the disclosed embodiments relate to a composite laminate structure 20 that is designed to enable non-destructive evaluation (NDE) of the integrity and condition of the laminate structure 20 by interrogating the structure 20 with electromagnetic (EM) energy 40. The NDE may include the detection of internal inconsistencies in or between layers 24 of the composite laminate structure 20 which will sometimes be referred to herein simply as a laminate 20. As used in this description, the term "inconsistencies" is intended to include a wide range of laminate conditions of interest, including but not limited to air bubbles, voids, ripples, waves in fiber alignment, balling or bunching of fibers, cracking, delamination, changes in materials and a variety of other variations, non-conformities and changes in structural properties that may occur as a result of an discrete event, or more slowly over a period of time. The layers 24 of the laminate 20 may comprise a fiber reinforced synthetic resin, such as without limitation, a carbon fiber reinforced epoxy.

NDE of the laminate 20 may be performed using apparatus generally indicated by the numeral 25. The apparatus 25 includes an EM energy generator 26 that generates EM energy of a preselected wavelength, which may or may not be polarized. The selected wavelength may vary, generally within microwave region, depending on the application, the construction of the laminate 20 and the types inconsistencies that may be of particular interest. In one application for example, the wavelength of the EM energy may be generally around the X-band, broadly in the range of about 5 mm to 50 mm. In other applications, the EM energy may be generated and transmitted on more than one wavelength (i.e. at multiple frequencies).

A combined transmitter/receiver 28 functions both to transmit an EM energy radiation beam 40 onto the laminate and to receive reflected radiation from the laminate 20. The receiver/transmitter may comprise for example, and without limitation, a conventional waveguide (not shown) having a highly directive aperture suitable for the application. When a single waveguide is employed for transmission and reception, the transmitter and receiver may be alternately switched at a relatively rapid rate to alternately transmit and receive EM radiation. Alternatively, separate waveguides (not shown) may be used to simultaneously transmit and receive the EM radiation. A scanner 30 may be coupled with the receiver/transmitter 28 to cause the transmitter/receiver 28 to scan 42 the beam 40 across the laminate 20 in a predetermined pattern, such as a raster pattern, in order generate a series of electrical signals representing a reflected image of the laminate 20, also referred to hereinafter as a reflected signature. In some embodiments, the scanning of the beam 40 may be performed electronically.

The apparatus 25 may further include a data processing system 32 comprising a computer 34, a display and one or more electronic databases 36. The computer 34 compares the received image of the laminate 20 represented by the reflected EM energy, and compares it to reference standards forming part of the database 36. These reference standards, also hereinafter referred to as design signatures, may include, but are not limited to, a database of electromagnetic properties that are a function of microwave wavelength for a broad range of polymer resins used to fabricate the laminate 20. The display 38 may be used to display an image of consistencies that are revealed by comparing the reflected EM energy with the reference standards stored in the database 36.

Figure 2:
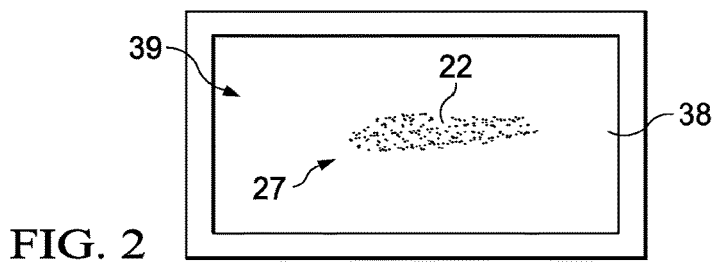
FIG. 2 is a front view of a display forming part of the apparatus shown in FIG. 1, illustrating an image of an inconsistency in the laminate.

FIG. 2 in an enlarged view of the display 38 in which an inconsistency 22 is represented by a darkened area 27 in a lighter and otherwise image-free surrounding background 39. In this example, the image-free background 39 results from a lack of refection of the EM radiation incident on the anti-reflective laminate 20 which is designed to be substantially anti-reflective of EM radiation of the selected EM wavelength. Alternatively, where the laminate 20 is designed to be substantially completely reflective of the incident EM radiation, the area 27 representing the inconsistency 22 would be relatively light and the surrounding background would be comparatively dark. Although not shown in the Figures, it is possible to use the reflected EM energy to map inconsistencies 22 in three rather than two dimensions, thus providing information about the depth and contours of the inconsistencies 22, as well as their locations within the area of the laminate 20 being scanned.

Figure 3:
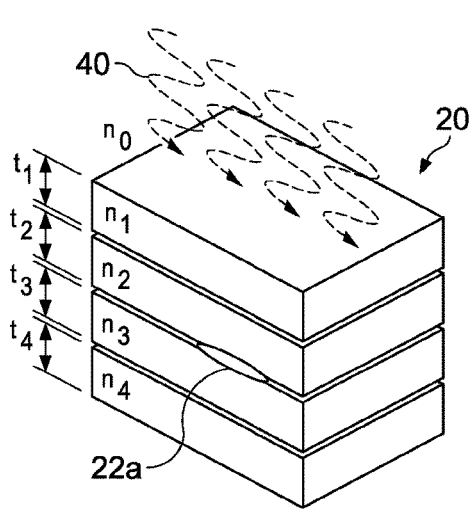
FIG. 3 is a perspective view of an anti-reflective composite laminate containing an inconsistency.

FIG. 3 illustrates a typical composite laminate comprising a stack of multiple layers $n_1$-$n_4$ having respective thicknesses $t_1$-$t_4$. As previously discussed, the laminate 20 is interrogated by EM radiation 40 of a preselected wavelength to determine whether there may be one or more inconsistencies in the laminate 20, such as a delamination 22a shown between layers $n_2$ and $n_3$. As part of the laminate design process, the composite laminate 20 is structured as a multilayer, anti-reflective "optical" stack resonant at the specified wavelength of the EM radiation, and may, but need not be particularly sensitive to phase or polarization of the EM energy.

At least two alternating layers $n_1$-$n_4$ of the laminate 20 are formed of differing materials, as will be discussed in more detail below. Because the laminate 20 is normally optically anti-reflective of the incident EM radiation 40, even slight inconsistencies 22 such as the delamination 22a that are even less in size than the wavelength of the EM radiation 40 disrupt the optical properties of the laminate 20. These optical disruptions are effectively imaged in the EM energy that is reflected from the laminate 20 back to the receiver/transmitter 28 (FIG. 1). In a similar manner, the layers $n_1$-$n_4$ may be designed to create an optical laminate stack 20 that is substantially completely reflective of the incident EM radiation. Again, inconsistencies 22 cause disruptions in the optical properties of the laminate 20, and these disruptions effectively suppress reflection of EM energy back to the receiver/transmitter 28 (FIG. 1) in the area of the inconsistency.

As is well known, if the thickness of the first layer $n_1$ shown in FIG. 3 is:

$$t_1 \approx \frac{\lambda}{4n_1} \qquad (1)$$

where $\lambda$ is the wavelength of the EM radiation, then the first layer $n_1$ presents an anti-reflection coating to the second layer $n_2$ if the indices of refraction of the layers at the center wavelength are related by:

$$n_1 = \sqrt{n_0 n_2} \qquad (2)$$

Furthermore, in order for the radiation to penetrate the first layer $n_1$, either due to off-axis effects or to small variations in the index of refraction, then the second layer $n_2$ can itself act as an antireflection coating to the third layer $n_3$ if it has a thickness of:

$$t_2 \approx \frac{\lambda}{4n_2} \qquad (3)$$

and an index of refraction related to its neighbors by:

$$n_2 = \sqrt{n_1 n_3} \qquad (4)$$

The disclosed laminate and NDE method is sensitive to defects because defects lead to changes in the thickness or in the indices of refraction of the layers of the laminate that affect this performance. To illustrate this principal, consider the general reflection coefficient for a ¼ quarter-wave wave antireflection layer:

$$R_1 = \frac{(n_0 n_2 - n_1^2)^2}{(n_0 n_2 + n_1^2)^2} \qquad (5)$$

The change in the index of refraction due to a quarter wavelength sized bubble (inconsistency) in the laminate 20 will be approximately n/4 over one wavelength. The change in the reflectivity in this region will be approximately:

$$R_1 \approx \frac{\left(n_0 n_2 - n_1^2\left(1 - \frac{1}{4}\right)\right)^2}{\left(n_0 n_2 + n_1^2\left(1 - \frac{1}{4}\right)\right)^2} \approx \frac{\left(\frac{15}{16}\right)^2}{\left(\left(2 - \frac{1}{2} + \frac{1}{16}\right)\right)^2} = \left(\frac{3}{5}\right)^2 = 0.36 \qquad (6)$$

where $n_0$, $n_1$ and $n_2$ are the nominal values around the bubble. The reflectivity due to a ¼ wavelength void changes from zero to 36%, which constitutes a relatively high contrast change in the response of the system due to a small change in the material parameters.

If the entire composite laminate 20 is approximately 1 centimeter thick for example, and is composed of four layers $n_1$-$n_4$, and the indices of refraction of these layers are in the range of 1.4 to 2.4, then it is apparent that the relevant wavelengths of applicability are approximately X-band microwave (the ultimate resolution in this particular example is a few millimeters). If each of the layers $n_1$-$n_4$ is thinner, or if the number of layers is greater, then the appropriate microwave frequency to be used for the interrogation increases and the ultimate resolution gets better. The opposite is true as well; for example, assume the laminate 20 consists of ½ wavelength thick layers $n_1$-$n_4$, or Equation (1) was modified to be:

$$t_1 \approx \frac{\lambda}{2n_1} \qquad (7)$$

Then the reflected EM energy would be nearly maximal at the EM wavelength of interest, and the change in material properties would result in a decrease in the reflectivity, instead of an increase.

The design of the periodic stacked laminate 20 to minimize or maximize the reflectivity (i.e. reflected EM energy) at a particular wavelength can be modified in several ways to: (1) require multiple layers in the laminate 20 to achieve full reflectivity cancellation or enhancement over a wide range of incident angles, and to increase the sensitivity to lower layers, or (2) require multiple layers in the laminate 20 to broaden the wavelength range where reflectivity cancellation or enhancement occurs, to loosen the sensitivity to lower layers. For example, indices of refraction of layers $n_1$, $n_2$, $n_3$, and $n_0$ may be different from one another. For example, a double layer quarter wavelength laminate 20 (with thickness as in equations (1) and (3) above) may have indices of refraction chosen to satisfy the equation.

The indices of refraction of layers $n_1$ and $n_2$ must both satisfy the stringent requirements at sub-wavelength length scales in order to achieve the cancellation of the reflectivity to EM radiation. Deviations from the requirements in either layer $n_1$, $n_2$ may substantially adversely affect performance. These principals may be extended to a laminate 20 having any number of layers. Computer computation may be employed to calculate the parameter values needed to provide optimum results for a given laminate and practical application.

The approximate thickness of the layers $n_1$-$n_4$ determines selection the particular EM wavelength employed to practice the disclosed NDE method. The layer thicknesses and the EM wavelengths are related to the indices of refraction according to:

$$t_i = \frac{\lambda}{n_i}\left(k + \frac{1}{4}\right), k = 0, 1, 2, \ldots \qquad (9)$$

Figure 4:
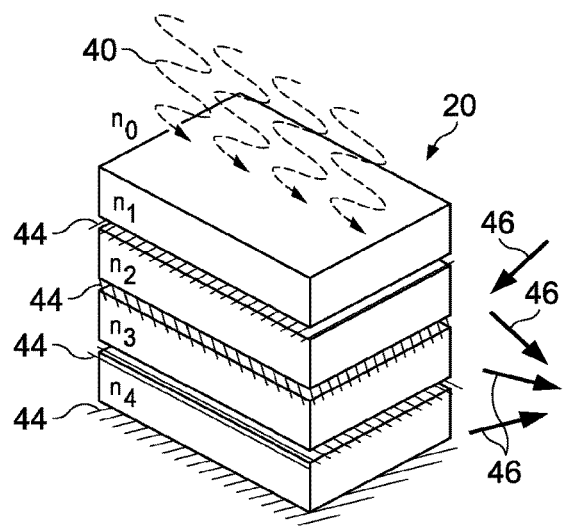
FIG. 4 is a view similar to FIG. 3 but illustrating the orientation of unidirectional reinforcement fibers between the layers of the laminate.

Referring now to FIG. 4, the composite laminate may include unidirectional reinforcement fibers 44, such as, without limitation, carbon fibers. In the illustrated embodiment, the unidirectional reinforcement fibers 44 have sequentially differing fiber orientations between the layers $n_1$-$n_4$ of the laminate 20. The reinforcing fibers 44 are laid between the anti-reflective layers $n_1$-$n_4$ with orientations 46 that rotate according to the thickness of the layer $n_1$-$n_4$ at angles appropriate for a traditional quarter wavelength laminate 20. In one embodiment, the reinforcing fibers 44 of alternating ones of the layers $n_1$-$n_4$ are arranged substantially perpendicular to each other. Reinforcing fibers 44 formed of materials that interact strongly with EM radiation, such as carbon, may be arranged during the layup process to minimize this interaction at a specific EM wavelength, polarization and phase, thereby allowing the EM radiation to penetrate the entire depth of the laminate 20. The laminate 20 may be anti-reflective at a given phase.

The anti-reflecting properties of the laminate 20 will provide a reflected signal that can be analyzed to detect inconsistencies even when the EM radiation is not polarized, although the resulting image contrast may be less than that when using polarized EM radiation to interrogate the laminate 20. It may be particularly desirable to employ EM radiation that is circularly polarized, since the electric field vector of the radiation is constantly turning in a circle as it propagates through the laminate 20. This turning of the electric field vector results in the field being oriented substantially perpendicular to the linear orientation of the reinforcing fibers 44 as the radiation propagates through each layer of the laminate 20.

Figure 5:
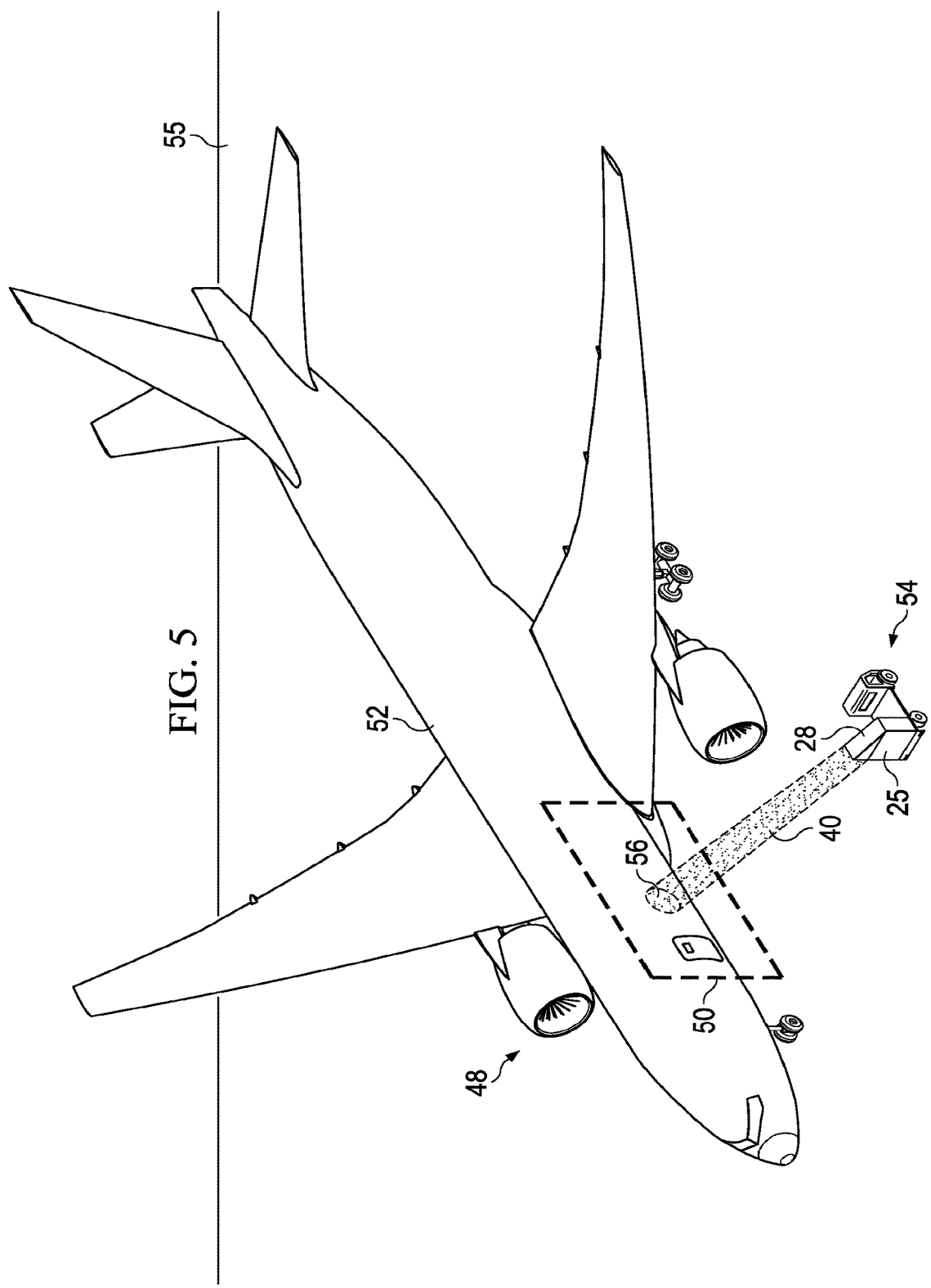
FIG. 5 is a perspective view of an aircraft having a composite laminate skin being evaluated using the apparatus of FIG. 1.

Attention is now directed to FIG. 5 which illustrates an aircraft 48 having a fuselage 52 formed of a composite laminate designed and manufactured according to the disclosed embodiments. The disclosed NDE method may be used to initially qualify the aircraft 48 for service, and thereafter to requalify it in situ from time-to-time after it has been placed in service. The NDE apparatus 25 previously described in connection with FIG. 1, may be mounted on a ground service vehicle 54 allowing the apparatus 25 to be moved to various positions on a tarmac 55 around the aircraft 48. The transmitter/receiver 28, which may comprise a single EM waveguide or separate waveguides (not shown), is used to scan one or more laminate components of the aircraft.

In the illustration shown in FIG. 5, a generally rectangular area 50 of the fuselage 52 is being scanned by an EM radiation beam 40 directed as a spot 56 onto the fuselage 52 which is moved over the area 50 under evaluation in a suitable pattern, such as a raster pattern. In one practical application, the spot 56 may be approximately one meter in diameter and the power of the radiation beam 40 may be on the order of several hundred watts. Where less power is available to generate the radiation beam 40, the spot 56 may have a smaller diameter. In this example, the EM radiation is a dual frequency, circularly polarized beam 40 in the microwave wavelength region, which produces dual frequency back-reflected (or back-suppressed reflected) signatures that are received and processed by the apparatus 25 on board the vehicle 54. The fuselage laminate is formed of a lamina stack that is resonant at the two frequencies of the interrogating EM beam 40. As previously discussed, resonance of the lamina stack at these two frequencies is achieved through an engineered selection of the lamina thicknesses and resins. The phase of the reflected EM energy may provide an indication of the depth of any detected inconsistencies 22.

Figure 6:
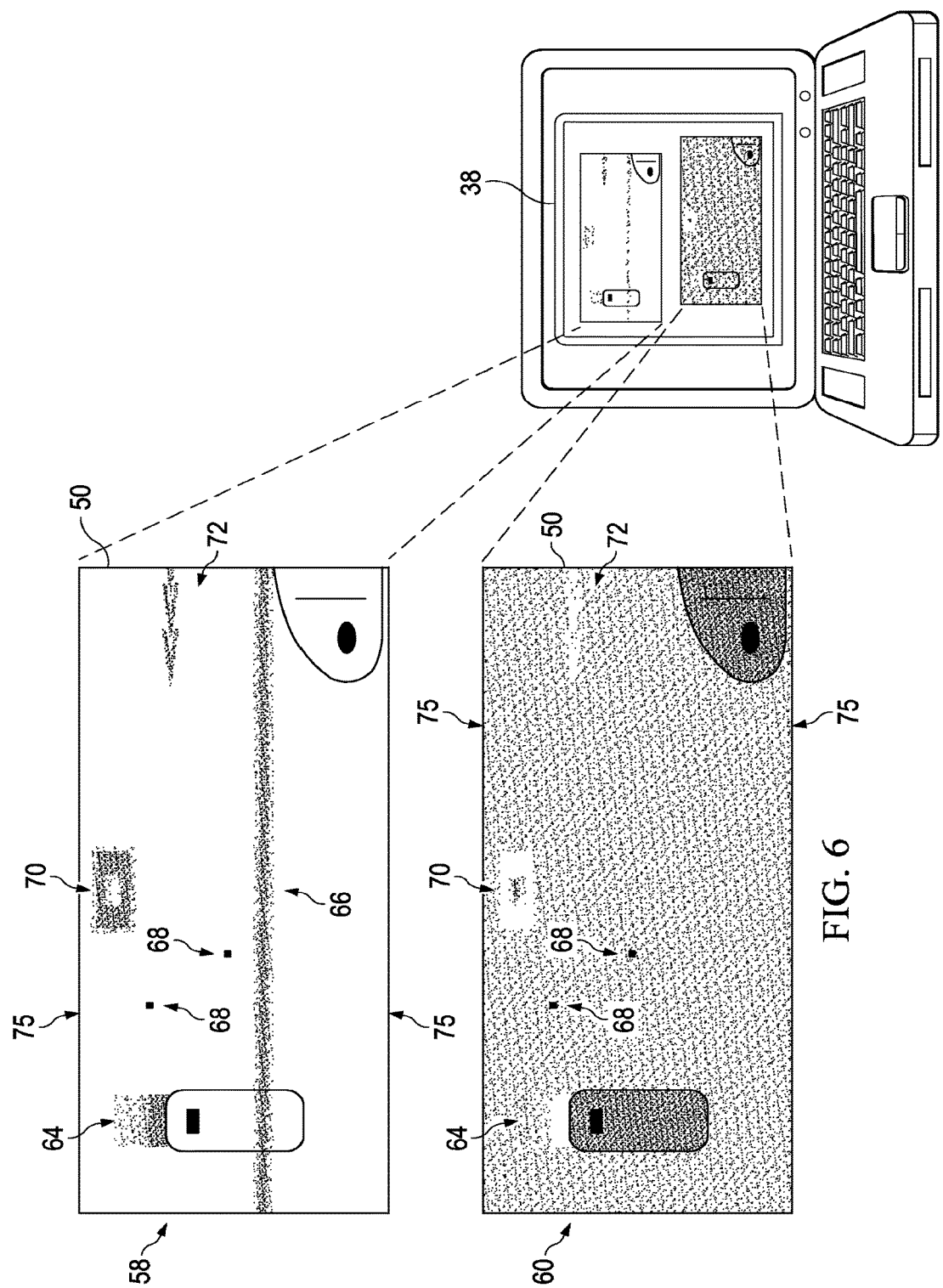
FIG. 6 is a diagrammatic illustration showing the results of the evaluation the aircraft shown in FIG. 6.

FIG. 6 illustrates one possible set of results of scanning the fuselage area 50 of FIG. 5 with EM radiation at two different design frequencies. The scanning process results in back-reflected EM energy from the fuselage area 50 at two different frequencies that are preselected based on the engineering design characteristics of the fuselage laminate. Using the principals of the disclosed embodiment, the laminate forming the fuselage 52 may be designed to be completely anti-reflective of EM radiation at a particular wavelength, polarization and phase, as previously discussed, or completely reflective of the EM radiation. In either case, a "clean" reflection background is provided against which inconsistencies in the laminate become visible. As previously discussed, the data processing system 34 compares the signature of the reflected EM energy at each of the two frequencies with design signatures forming part of the electronic database 36, and also compares the two frequency responses to each other in order to identify possible inconsistencies in the laminate and provide a visual 2-D map of the scanned area 50 showing the location and extent of any inconsistencies 22.

In FIG. 6, 64 indicates an area containing possible delamination, while 68 indicates areas that may contain small impact damage. Areas that have become thicker or thinner over time are shown at 70. An area containing possible fiber bunching or distortion is shown at 72. 75 represents the effects of curvature of the fuselage 52, and 66 indicates a reflection cause by paint "glint". The upper image 58 represents the scanned response at the first design frequency, and the lower image 60 represents the response of scanning at the second design frequency.

Figure 7:
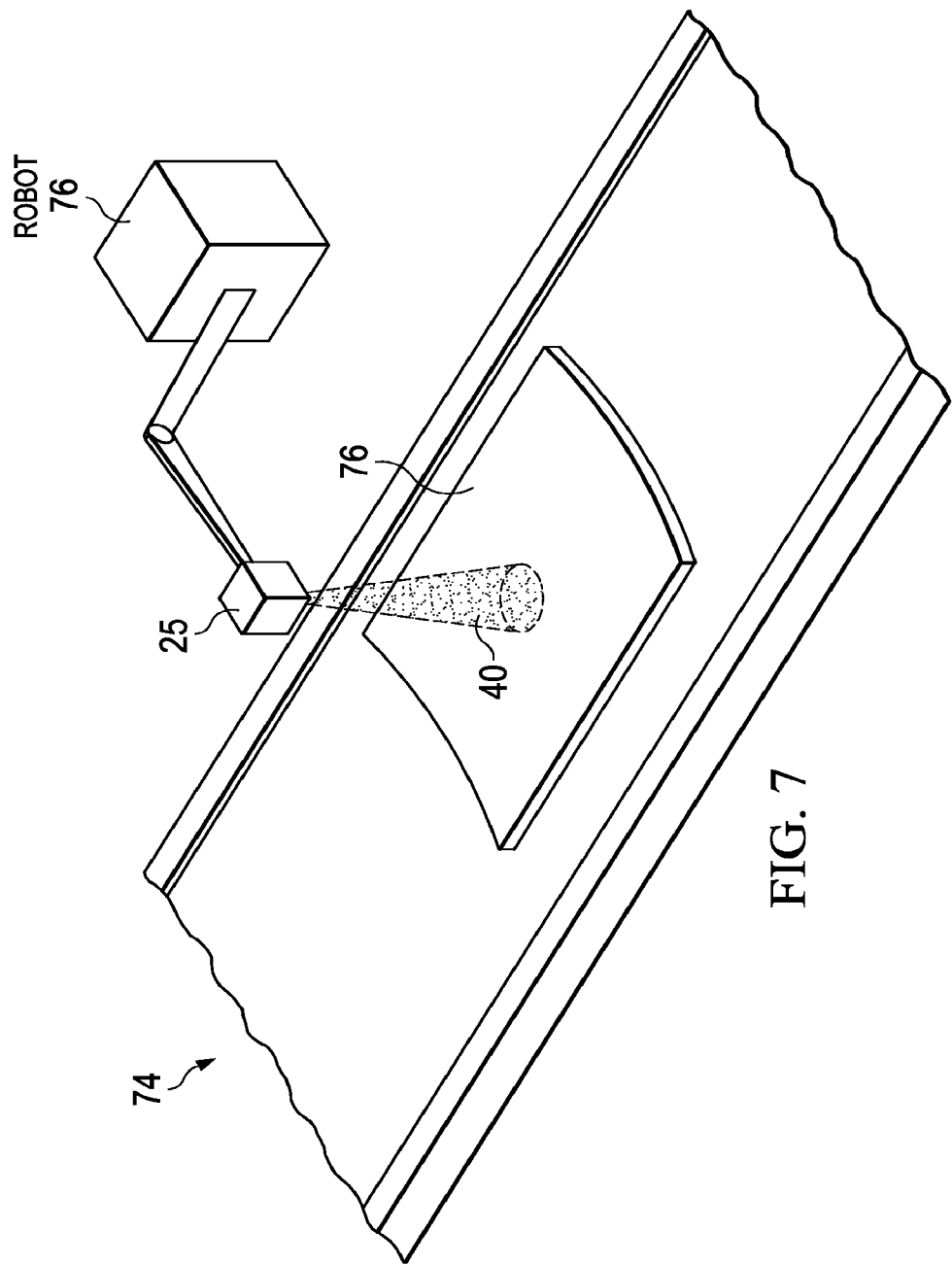
FIG. 7 is a perspective view of a portion of an aircraft skin being evaluated using the disclosed apparatus.

As previously mentioned, the disclosed laminate and NDE method may be employed to evaluate composite laminate components of a structure at the time they are manufactured, and before they are assembled and/or placed in service. For example, FIG. 7 illustrates a manufacturing environment 74 in which a composite laminate wing skin 76 is being evaluated for inconsistencies before being assembled with other components of a wing. The NDE apparatus 25 shown in FIG. 1 may be mounted on a robot 76 that scans the EM beam 40 over the skin 76. The results of the evaluation may be used by manufacturing personnel to determine whether rework of the skin or changes in production processes may be necessary.

Figure 8:
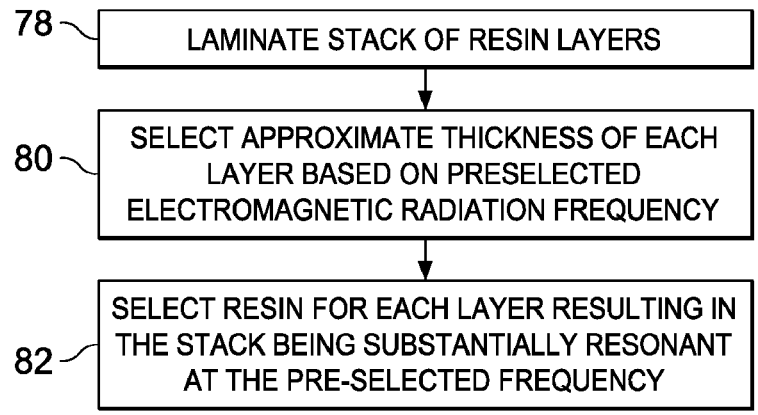
FIG. 8 is a flow diagram of one embodiment of a method of manufacturing a composite laminate enabling non-destructive evaluation of the laminate using electromagnetic radiation.

Attention is now directed to FIG. 8 which illustrates one embodiment of a method of manufacturing a composite laminate enabling detection of inconsistencies. Beginning at step 78, stack of resin layers is laminated, and at 80, the approximate thickness of each of the resin layers is selected based on a preselected electromagnetic radiation frequency. At 82, a resin is selected for each of the resin layers that results in the stack being substantially resonant at the preselected frequency.

Figure 9:
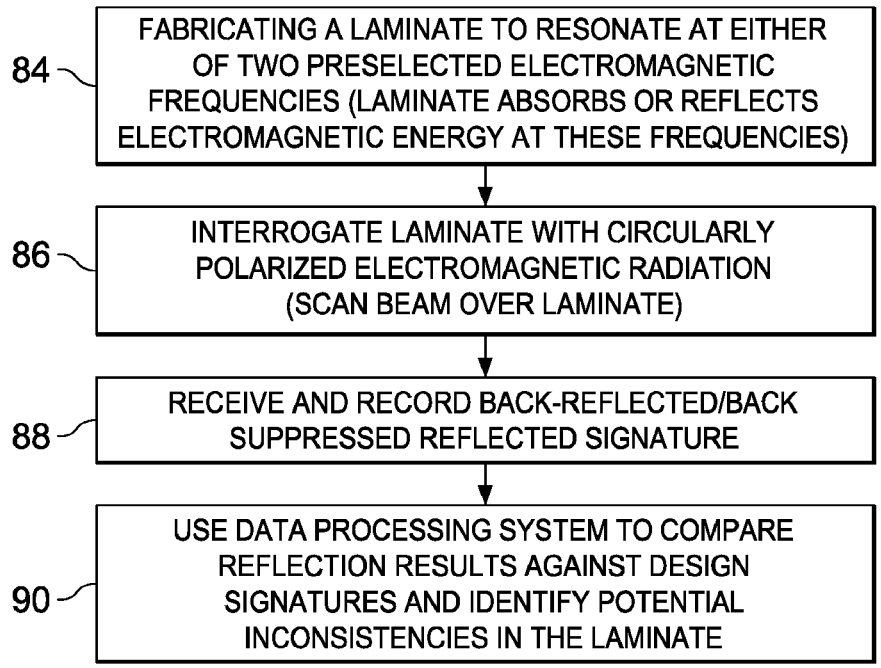
FIG. 9 is a flow diagram of an alternate method of manufacturing and non-destructively evaluating composite laminates according to the disclosed embodiments.

Attention is now directed to FIG. 9 which illustrates a method of detecting inconsistencies in composite laminates. Beginning at 84, a laminate 20 is designed to resonate at either of two preselected electromagnetic frequencies, at which frequencies the laminate 20 either absorbs or reflects electromagnetic energy. At 86, the laminate 20 is interrogated with circularly polarized electromagnetic radiation, which includes scanning a beam of the radiation over the laminate 20. At 88, a back-reflected signature or back-suppressed signature is received from the laminate 20 and recorded. At 90, a data processing system is used to compare the reflected signature against design signatures and identify potential inconsistencies in the laminate.

Further, different advantageous embodiments may provide different advantages as compared to other advantageous embodiments. The embodiment or embodiments selected are chosen and described in order to best explain the principles of the embodiments, the practical application, and to enable others of ordinary skill in the art to understand the disclosure for various embodiments with various modifications as are suited to the particular use contemplated.

What is claimed is:

1. A method for enabling structural monitoring using electromagnetic radiation, the method comprising:
   providing a source of electromagnetic radiation; and
   providing a composite laminate in an aircraft fuselage comprising:
   a first portion comprising a laminated stack of resin layers and unidirectional reinforcement fibers between the resin layers, the first portion having a depth, wherein each of the resin layers has an index of refraction between 1.4 and 2.4, wherein the first portion is anti-reflective to a wavelength of an electromagnetic radiation of a microwave X-band between 5 mm and 50 mm; and a second portion consisting of an inconsistency that is located within the first portion and that is reflective to the wavelength;

wherein the wavelength of the electromagnetic radiation penetrates the depth of the first portion except where it encounters the second portion and is reflected by the second portion.

2. The method of claim 1, further comprising:

wherein an approximate thickness of each of the resin layers is based on a preselected electromagnetic radiation frequency; and wherein the laminated stack of resin layers has a resonance at the preselected electromagnetic radiation frequency.

3. the method of claim 1, further comprising:

detecting and mapping the inconsistency.

4. The method of claim 1, wherein the inconsistency is an air bubble.

5. The method of claim 1, wherein the inconsistency is a void.

6. The method of claim 1, wherein the inconsistency is a ripple.

7. The method of claim 1, wherein the inconsistency is a wave in fiber alignment.

8. The method of claim 1, wherein the inconsistency is a balling or a bunching of fibers.

9. The method of claim 1, wherein the inconsistency is a cracking.

10. The method of claim 1, wherein the inconsistency is a delamination.

11. The method of claim 1, wherein the inconsistency is a change in material.

12. The method of claim 1, wherein the inconsistency is a change in a structural property.

13. The method of claim 1, wherein the resin layers in the laminated stack of resin layers are stacked on top of each other.

14. The method of claim 1, wherein each of the resin layers has an approximate thickness that is based on a preselected electromagnetic radiation frequency.

15. The method of claim 1, wherein orientations of the unidirectional reinforcement fibers between the resin layers are sequenced in the laminated stack.

16. The method of claim 15, wherein, wherein the orientations of the unidirectional reinforcement fibers are determined by a frequency of the electromagnetic radiation.

17. The method of claim 1, wherein the unidirectional reinforcement fibers are between alternating resin layers.

18. The method of claim 1, wherein the unidirectional reinforcement fibers are oriented generally perpendicular to each other.

19. The method of claim 1, wherein the unidirectional reinforcement fibers include carbon.

20. The method of claim 1, wherein the resin layers include epoxy.

21. The method of claim 2, wherein the inconsistency, wherein the inconsistency in the second portion disrupts the resonance at the preselected electromagnetic radiation frequency.

* * * * *